US008246610B2

(12) United States Patent
Riedel et al.

(10) Patent No.: US 8,246,610 B2
(45) Date of Patent: Aug. 21, 2012

(54) APPARATUS, METHOD AND CONTROL PROGRAM FOR OPHTHALMOLOGICAL, IN PARTICULAR, REFRACTIVE LASER SURGERY

(75) Inventors: Peter Riedel, Nürnberg (DE); Christof Donitzky, Eckental (DE)

(73) Assignee: Wavelight AG, Erlangen (DE)

( * ) Notice: Subject to any disclaimer, the term of this patent is extended or adjusted under 35 U.S.C. 154(b) by 293 days.

(21) Appl. No.: 12/603,983

(22) Filed: Oct. 22, 2009

(65) Prior Publication Data
US 2010/0106143 A1 Apr. 29, 2010

Related U.S. Application Data

(63) Continuation of application No. PCT/EP2008/005332, filed on Jun. 30, 2008.

(51) Int. Cl.
*A61B 18/20* (2006.01)
(52) U.S. Cl. .................... 606/5; 606/4; 606/10
(58) Field of Classification Search .............. 606/4–6, 606/10–12; 351/205–212; 128/898
See application file for complete search history.

(56) References Cited

U.S. PATENT DOCUMENTS

| 6,099,522 | A | * | 8/2000 | Knopp et al. | 606/10 |
| 6,159,202 | A | * | 12/2000 | Sumiya et al. | 606/4 |
| 6,726,680 | B1 | | 4/2004 | Knopp et al. | |
| 2004/0143246 | A1 | | 7/2004 | Maeda et al. | |
| 2009/0275929 | A1 | * | 11/2009 | Zickler | 606/5 |

FOREIGN PATENT DOCUMENTS
WO 2007143111 A2 12/2007

OTHER PUBLICATIONS

Patent Cooperation Treaty—European Patent Office, "Notification of Transmittal of the International Search Report and the Written Opinion of the International Searching Authority, or the Declaration," International Application No. PCT/EP2008/005332, Apr. 6, 2009, 13 pages.

* cited by examiner

*Primary Examiner* — Ahmed Farah
(74) *Attorney, Agent, or Firm* — Haynes and Boone, LLP

(57) ABSTRACT

Disclosed is an apparatus for ophthalmological, in particular, refractive laser surgery, which aligns a required ablation profile on a specified corneal point, which it calculates from the image data of an eye tracker, taking account of the depth of the anterior chamber of the eye, including the depth of the cornea, calculated individually for the respective patient.

13 Claims, 2 Drawing Sheets

Figure 1:
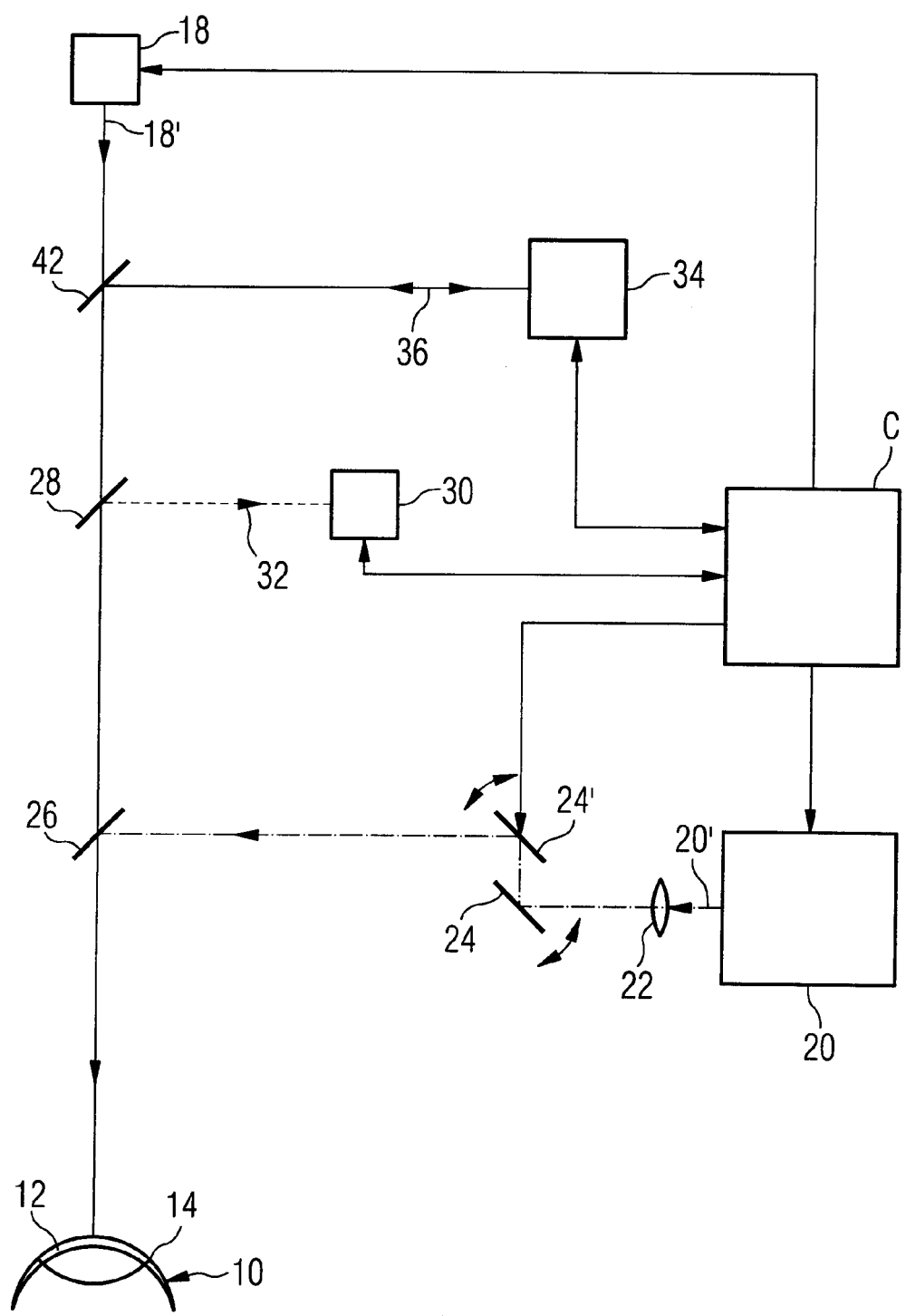

APPARATUS, METHOD AND CONTROL PROGRAM FOR OPHTHALMOLOGICAL, IN PARTICULAR, REFRACTIVE LASER SURGERY

CROSS-REFERENCE TO RELATED APPLICATION

This application is a United States Continuation application of co-pending international patent application number PCT/EP2008/005332, filed Jun. 30, 2008, the disclosure of which is incorporated herein by reference.

This application is a United States Continuation application of co-pending international patent application number PCT/EP2008/005332, filed Jun. 30, 2008, the disclosure of which is incorporated herein by reference.

The invention relates to an apparatus for ophthalmological, in particular, refractive laser surgery. It relates, further, to a control program for such an apparatus, and to a method for generating such a control program.

Here, refractive laser surgery is to be understood as the alteration of the imaging properties of the optical system "eye" by means of laser radiation. The interaction of the incident laser radiation with the eye alters the refractive properties of one or more components of the eye. Since the imaging properties of the eye are determined primarily by the cornea, in many cases refractive laser eye surgery involves treatment of the cornea. In such treatment, specific application of incisions and/or specific removal of material effect(s) alteration of the shape of the cornea; the term reshaping is therefore also used.

A prominent example of reshaping of the cornea for the purpose of altering its refractive properties is that of LASIK (laser in-situ keratomileusis). In the case of LASIK, a small, superficial wafer, commonly termed a flap in the specialist field, is first cut out of the cornea. The flap remains attached, at a portion of its edge, to the adjoining corneal tissue, such that it easily be folded to the side and subsequently folded back again. In practice hitherto, two methods, in particular, are used for producing the flap, being, on the one hand, a mechanical method, by means of a microkeratome, and, on the other hand, a laser-technics method, wherein, by means of femtosecond laser radiation (i.e. pulsed laser radiation with a pulse duration in the fs range), a flat, sub-surface incision is made in the cornea, which incision is brought outwards, apart from the region of the hinged joint to the surface of the cornea. After the produced flap has been folded away, removal of material (ablation) from the thus exposed stroma is effected, in accordance with a predefined ablation profile. The ablation profile specifies how much tissue is to be removed at which location of the cornea. The ablation profile is so calculated that, following the ablation, the cornea has an optimum shape for the treated eye and the previously existing optical imaging defects of the eye are, as far as possible, corrected. Appropriate methods have long been available to the specialist field for calculation of the ablation profile. For example, an excimer laser, having a radiation wavelength in the UV range, at approximately 193 nm, is used for the ablation.

Once the ablation profile has been determined for the eye that is to be treated, it is then calculated how the required removal can best be achieved with the available laser radiation. The laser radiation used is normally pulsed radiation. It is therefore a matter of calculating, according to space and time, a sequence of laser pulses that, in interaction with the cornea, in particular the stroma, effect the required reshaping of the cornea.

Beam guidance means, for so guiding a laser beam over the eye to be treated that the required sequence of laser pulses in space and time is achieved, are known per se in the prior art. In particular, the beam guidance means can comprise a deflection unit, also known as a scanner, which serves to deflect the laser beam in the transverse direction (x-y direction), as well as focussing optics, for focussing the laser beam at a required height position (z direction). The deflection unit can comprise, for example, one or more galvanometrically controlled deflection mirrors.

The present invention is not restricted to LASIK technics. it can also be applied in the case of other laser surgical operations on the eye, for instance in the case of PRK (photorefractive keratectomy), LASEK, EPI-LASIK, or in the case of incisional procedures, in which only incisions are made in the cornea. Moreover, the invention is also not restricted to treatment of the cornea by laser surgery; application of the invention for treatments of the lens, for example, are also conceivable.

The mentioned beam guidance means are controlled by means of a program-controlled computer, in accordance with the ablation profile—or, more generally, in accordance with a treatment profile. If the treatment is a non-ablative surgical treatment, the treatment profile can also, for example, be an incision profile that specifies at which location, and how deeply, an incision is to be made.

The treatment profile requires a reference point, to which the sequence of the laser points is spatially related. It has been proposed, particularly in connection with LASIK ablation, that the mid-point of the pupil be used as a reference point for the ablation profile. The pupil is the opening that is left open by the iris diaphragm, and through which radiation passes into the eye and onto the retina; it has a relatively sharp contour, and therefore it is suitable for being photographed by means of a camera and evaluated by means of image processing programs. Appropriate camera technology and processing programs are available in the prior art.

The human eye, however, is not a stationary object, but one that executes movements continually. There are various types of eye movements, some of which are executed on differing timescales. Of importance only is the determination that the eye is never still. This applies even when it is attempted to fix the view upon a particular specified object; even then, unavoidable fixation movements occur. Since the pupil participates in the mentioned eye movements to a greater or lesser extent, the eye can be tracked, in respect of its movements, through observation or monitoring of the pupil by camera. Corresponding eye tracking devices (eye trackers) track movements of the eye by taking sequences of images of the pupil, including the surrounding iris, and subsequent evaluation of the image sequences by means of software. In the context of image evaluation, it is the instantaneous location of the pupil centre, in particular, that is determined. Since the ablation centre (centre of the ablation profile) is always re-aligned on the thus determined pupil centre, the required spatial sequence of laser pulses can be reliably directed onto the correct locations of the eye region to be treated.

The use of the pupil centre as a reference point for the ablation profile is associated with a systematic disadvantage, however, since it does not take account of the depth of the anterior chamber of the eye, located in front of the pupil, and also does not take account of the thickness of the cornea. Eye movements are generally rotational movements, the point of rotation being located within the vitreous body. If the eye moves by a certain angle, the pupil centre is displaced, in the pupil plane, by a first value, while a point located on the surface of the cornea is displaced, in the corneal plane, by a second value, which is greater than the first value, owing to the greater distance of the corneal point from the point of rotation in comparison with the distance between the pupil centre and the point of rotation. In the presence of eye movements, therefore, alignment of the ablation profile on the pupil centre results in inaccuracies.

Consideration may therefore be given to using, instead of the pupil centre, as a reference point for the ablation profile, a patent-specific point on the cornea that has a fixed spatial relationship to the pupil centre. In particular, in this case consideration may be given to the point at which the pupil axis pierces through the surface of the cornea. The pupil axis extends through the pupil centre and through the surface of the cornea. In the case of corneal treatments, use of a point located on the cornea as a reference point for the treatment profile makes it possible to avoid the mentioned systematic error that is encountered if, instead, a point located at a distance from the cornea, such as, for instance, the pupil centre, is used as a reference point.

For the purpose of calculating geometrically, from the pupil centre, a processing centre located on the cornea, there is a need for information concerning the rotational radius of the eye and the radial distance between the two centres. The latter is determined mainly through the depth of the anterior chamber of the eye; a small portion of this radial distance is further determined by the thickness of the cornea.

The invention proceeds from the knowledge that the depth of the anterior chamber, including the thickness of the cornea, can vary to an extent from person to person, that, to the end of improving the operation result, it is advantageous to ascertain metrologically in a definite manner, individually for the respective patient, the depth of the patient's anterior chamber (including the thickness of the cornea, if required), and to take this measured value into account in calculating the corneal processing centre from the position of the pupil centre. For example, in the case of a test group of patients, it could be ascertained that the depth of the anterior chamber, including the thickness of the cornea, varied between approximately 2.8 and 4.5 mm within the test group. In view of this ascertained breadth of variation, it is an aspect of the teaching according to the invention that it is possible that the assumption of a standard value, for example 3.5 mm, for the depth of the anterior chamber, including the thickness of the cornea, might not be very appropriate to the actual conditions in the case of a current patient, and therefore there is a continuing need to assume a comparatively large error if the processing centre is calculated from the pupil centre with the use of such a standard value.

The object of the invention is to disclose for ophthalmological, in particular, refractive laser surgery, a method by which, for a specified treatment profile, a reference point can be ascertained on the eye during treatment, which method enables improved operation results to be achieved.

According to the invention, there is provided for this purpose an apparatus for ophthalmological, in particular, refractive laser surgery, comprising
  a laser-beam source,
  beam guidance means for location- and time-controlled guidance of the laser beam, emitted by the laser-beam source, over an eye to be treated,
  a camera for taking an image of the iris and pupil of the eye,
  a program-controlled computer, connected to the camera, for controlling the beam guidance means in accordance with a treatment profile, the computer being set up to ascertain during the treatment of the eye, on the basis of the image data supplied by the camera, the position of a specified point on the cornea of the eye and to align the treatment profile relative to the thus ascertained position of the corneal point.

According to the invention, the apparatus in this case is equipped with a measuring device for measuring a depth dimension of the eye to be treated, which depth dimension is representative of the depth of the anterior chamber and, if required, of the thickness of the cornea, the computer being supplied with the measurement data of the measuring device, and being set up to ascertain the position of the specified corneal point, taking account of the measured depth dimension.

The invention thus teaches that the depth of the anterior chamber and, if required, the thickness of the cornea be measured individually for the respective patient, and the laser processing be aligned on a corneal point that has been ascertained with these measured values having been taken into account. Preferably, the reference point is located on the front side of the cornea. The measurement can be performed immediately prior to commencement of the surgery.

Coherent optical interferometric measurement methods for contactless measurement of biological tissue, such as, for instance, optical coherence tomography (OCT), or coherence range reflectometry (OLCR: optical low coherence reflectometry) have been available for some time. These measurement methods operate with broadband radiation (e.g., SLED, ASE, supercontinuum laser), and allow biological structures to be measured with high resolution, down to the range of 1 μm and finer.

In a preferred development, the invention teaches that such a coherent optical interferometric measuring device be integrated into the laser surgical apparatus, the measuring device being, in particular, an OLCR measuring device. The high measuring accuracy of such a measuring device allows the variations of the depth of the anterior chamber and of the thickness of the cornea between different patients to be resolved and recorded with precision. The integration of the measuring device into the laser surgical apparatus is such that, in particular, the measuring beam emitted by the measuring device is directed onto the eye coaxially with the laser beam used for treatment, such that the patient need be positioned only once and, if necessary, the measurement can be repeated during the operation.

Not only the depth of the anterior chamber, but also the diameter of the eye as a whole, can differ from person to person. A differing eye diameter results in a correspondingly differing rotational radius in the case of rotational movements of the eye. Accordingly, in the case of a preferred embodiment, provision is made whereby the computer is set up to ascertain the position of the specified corneal point, with a patient-specific, preoperatively ascertained rotational radius of the eye also being taken into account. Taking into account the individually measured rotational radius allows further improvements in comparison with the use of a rotational radius that is specified as a standard.

As already mentioned, the point at which the pupil axis pierces through the surface of the cornea can be used as a specified corneal point. Alternatively, a corneal point that is in a fixed relative position in relation to this piercing point can be used.

In the case of LASIK interventions in particular, wherein the flap is first folded away, in order subsequently to perform the ablation, there is no possibility, during the ablation, of directly sweeping the surface of the cornea after a given point. Accordingly, the reference point for the ablation centre can only be calculated by indirect means. A possibility for this can consist in continuously ascertaining, during the laser treatment, from the image data of the camera, a current displacement dimension for the pupil centre that indicates the current position of the pupil centre in relation to a given reference position. The displacement dimension of the pupil centre can be determined, in particular, in the form of a displacement vector, which represents the direction and extent of the displacement of the pupil centre in relation to the reference position. Eye movements effected in the course of the laser intervention can then be expressed, respectively, by a displacement vector related to this reference position of the pupil centre.

Using the measured depth dimension, a displacement dimension, corresponding to the displacement dimension of the pupil centre, can then be calculated for the specified corneal point, for example, again in the form of a displacement vector. The current position of the specified corneal point can be calculated from the thus calculated displacement dimension of the specified corneal point and a known reference position for this point. Expediently in this case, the reference position of the specified corneal point is that position assumed by the specified corneal point when the pupil centre is in its reference position. For example, the position at which the pupil axis pierces through the surface of the cornea, and the associated position of the pupil centre, can be ascertained once, at the start of the operation, and stored as reference positions for the specified corneal point and the pupil centre.

The invention further provides a control program for an apparatus for ophthalmological, in particular, refractive laser surgery, the apparatus comprising a laser-beam source, beam guidance means for location- and time-controlled guidance of the laser beam, emitted by the laser-beam source, over an eye to be treated, a camera for taking an image of the iris and pupil of the eye, and a computer, which is connected to the camera and executes the control program, for controlling the beam guidance means in accordance with a treatment profile. The control program is designed in such a way that the computer ascertains during the treatment of the eye, on the basis of the image data supplied by the camera, the position of a specified point on the cornea of the eye and aligns the treatment profile relative to the thus ascertained position of the corneal point. The control program in this case ascertains the position of the specified corneal point taking account of a measured depth dimension of the eye to be treated, which depth dimension is representative of the depth of the anterior chamber and, if required, of the thickness of the cornea.

The control program can be stored, for example, on a machine-readable, portable data medium or in a memory chip that can be accessed by the computer.

Furthermore, the invention relates to a method for generating a control program for a program-controlled computer of an apparatus for ophthalmological, in particular, refractive laser surgery, the apparatus being set up to route laser radiation onto or into the eye according to a spatial and time sequence that is determined by a required treatment profile and that is aligned relative to a specified location of an eye to be treated. According to the invention, in the case of this method provision is made whereby a depth dimension of the eye to be treated is measured at least once prior to the surgery, which depth dimension is representative of the depth of the anterior chamber and, if required, of the thickness of the cornea, and the control program is so generated that, during the surgery, it ascertains the specified value of the eye, taking account of the measured depth dimension.

The disclosures made and preferred exemplary embodiments explained previously in connection with the laser surgical apparatus according to the invention apply, correspondingly, to the control program and the method.

Figure 2:
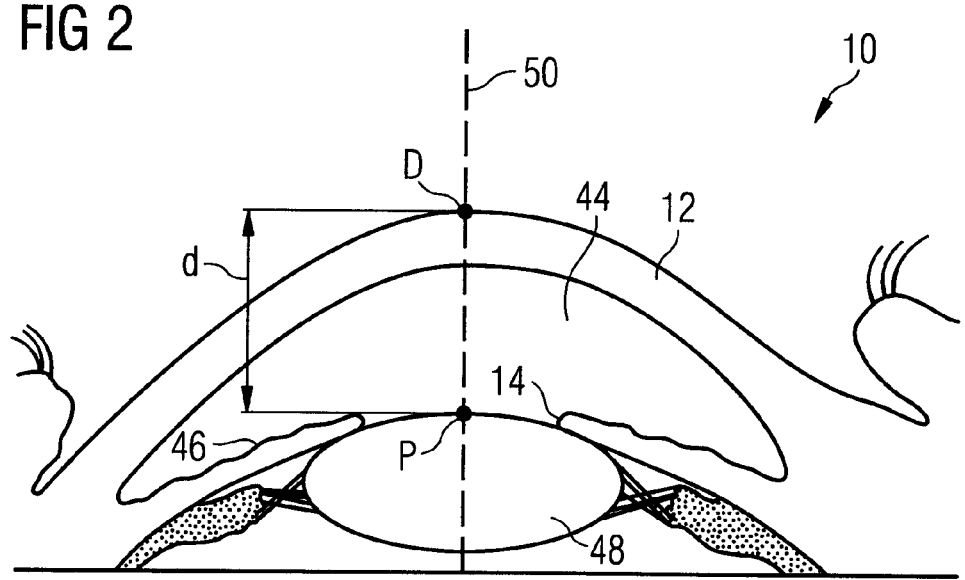
Figure 3:
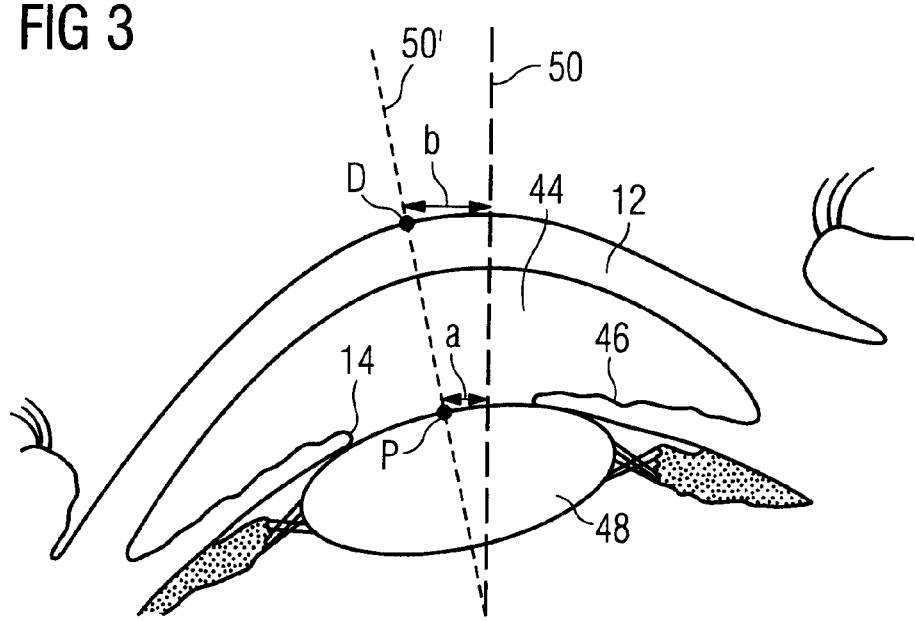

The invention is explained further in the following with reference to the appended drawings, wherein:

FIG. 1 shows a schematic block representation of an exemplary embodiment of an apparatus for refractive laser surgery of the eye, FIG. 2 shows a sectional representation of the front region of the eye, and FIG. 3 shows a sectional representation of the front region of the eye, in a position of the eye rotated relative to FIG. 2.

In FIG. 1, an eye to be treated with refractive laser surgery is indicated schematically at reference 10. The cornea of the eye 10 and the edge of the pupil are shown at 12 and 14, respectively.

The laser surgical apparatus according to FIG. 1 shows, in a manner known per se, a fixation light source (e.g. LED or laser) 18, which emits a (weak) fixation beam 18' and at which the patient's view is directed for the purpose of fixing the position of the eye.

The laser surgical apparatus further comprises a treatment laser 20, which emits treatment radiation 20' that is routed, via a lens 22, onto scanner mirrors 24, 24' and directed, via a deflection mirror 26, onto the eye 10. For a LASIK treatment, the laser 20 can be, for example, an excimer laser, the radiation wavelength of which is 193 nm. It is understood that other treatment wavelengths may also be used, if required, for other treatment purposes. A program-controlled computer C controls the laser 20 and the scanner mirrors 24, 24' according to a previously calculated treatment profile. It is assumed in the following that a LASIK treatment is performed by means of the surgical apparatus represented; accordingly, an ablation profile is assumed as a treatment profile.

The laser surgical apparatus additionally comprises a device for tracing eye movements (eye tracker). The eye tracker comprises a camera 30, by means of which images of the eye, specifically of the pupil and the iris, are taken, via a deflection mirror 28, in the direction of an arrow 32. The taken images are then evaluated in the computer C or in a preceding image processing unit, not represented, in order to track movements of the eye, which generally cannot be avoided by the patient, despite the attempted fixing of the view onto the fixation light 18'. The computer C takes account of the detected eye movements in controlling the scanner mirrors 24, 24', in order thus to keep the ablation profile aligned as constantly as possible in relation to a specified reference point on the surface of the cornea.

In addition, there is integrated into the laser surgical apparatus a measuring device 34 for OLCR (optical low coherence reflectometry), which device, in a manner known per se, includes a source for a measuring beam that is routed onto the eye 10 via a deflection mirror 42. Via the deflection mirror 42, and on the same path on which measuring radiation of the measuring device 34 is emitted, the measuring device 34 receives radiation reflected from the eye 10. This is indicated by a double arrow 36.

At the start of the LASIK, still before the flap is cut free and folded away, the measuring device 34 measures the depth of the anterior chamber of the eye, including the thickness of the cornea. Reference is now made to FIG. 2 in connection therewith. There, the anterior chamber of the eye is denoted by 44, 46 denoting the iris and 48 denoting the lens of the eye 10. The total dimension of the depth of the anterior chamber and the thickness of the cornea is denoted by d.

Further shown in FIG. 2 is a pupil axis 50, which joins a pupil mid-point P to a piercing point D, at which the pupil axis 50 pierces through the front surface of the cornea 12.

A rotation of the eye results in a displacement of the pupil axis 50 and also, accordingly, in a displacement of the pupil centre P and of the piercing point D. This situation is represented in FIG. 3. There, the new pupil axis is denoted by 50'. For comparison, the pupil axis 50 of the state according to FIG. 2 is shown. a and b denote distances by which the pupil centre P and the piercing point D, respectively, have been displaced relative to the state according to FIG. 2. It can be seen that, in the case of an eye movement, the piercing point D is displaced to a significantly greater extent than the pupil centre P, the difference between the displacement dimensions a, b being dependent on the depth of the anterior chamber 44 and the thickness of the cornea 12, i.e., in total, on the depth dimension d.

The computer C of the laser surgical apparatus aligns the ablation profile, not on the pupil centre P, but on the piercing point D as the ablation centre. For this purpose, it ascertains, for example, the position of the pupil centre P and the position of the piercing point D once, prior to commencement of the operation, and notes (stores) the thus ascertained values as reference positions. During the laser treatment, the computer C continuously ascertains the respectively current position of the pupil centre P on the basis of the image data of the camera 30, and calculates a displacement vector, which indicates the extent and direction of the displacement of the pupil centre P between the stored reference position and the current state. From the thus ascertained displacement vector for the pupil centre P, the computer C can calculate, on the basis of the measured depth dimension d and a rotational radius of the eye 10, which rotational radius is likewise obtained metrologically or specified as a standard, a displacement vector for the piercing point D. This calculation is possible by means of simple mathematics, for instance with the aid of the well-known intercept theorems of geometry. From the thus obtained displacement vector for the piercing point D and the stored reference position of this point, the computer C can then calculate the current position of the piercing point D. It is quite obvious that the amount of computation for these calculations is relatively small.

What is claimed is:

1. Apparatus for ophthalmological, refractive laser surgery, comprising:
   a laser-beam source;
   a beam guidance mechanism configured to control guidance of the laser beam, emitted by the laser-beam source, over an eye to be treated;
   a camera for taking an image of the pupil of the eye;
   a program-controlled computer, connected to the camera, for controlling the beam guidance mechanism in accordance with a treatment profile, the computer being set up to ascertain during the treatment of the eye, on the basis of the image data representative of the pupil supplied by the camera, the position of a specified point on the cornea of the eye and to align the treatment profile relative to the thus ascertained position of the corneal point;
   wherein a measuring device, supplying its measurement data to the computer, for measuring a depth dimension of the eye to be treated, which depth dimension is representative of the depth of the anterior chamber and the thickness of the cornea, the computer being set up to ascertain the position of the specified corneal point, taking account of the measured depth dimension, wherein the position of the specified corneal point is ascertained by determining a displacement of a center of the pupil relative to a reference position and calculating a corresponding displacement of the specified corneal point based upon the displacement of the center of the pupil relative to the reference position.

2. Device according to claim 1, wherein the measuring device is a coherent optical interferometric measuring device.

3. Device according to claim 1, wherein the computer is set up to ascertain the position of the specified corneal point by taking into account a rotational radius of the eye and a rotational displacement of the center of the pupil relative to the reference position.

4. Device according to claim 3, wherein the specified corneal point is the point at which the pupil axis pierces through the surface of the cornea, or is a point that is in a fixed relative position in relation to this piercing point.

5. Device according to claim 4, wherein the computer is set up to ascertain, from the image data of the camera, a displacement dimension for the pupil center, and to ascertain the position of the specified corneal point by calculating a corneal displacement vector based on the thus ascertained displacement dimension for the pupil center and the measured depth dimension.

6. An apparatus for ophthalmological, refractive laser surgery, the apparatus comprising:
   a laser-beam source;
   beam guidance mechanism configured to control guidance of the laser beam, emitted by the laser-beam source, over an eye to be treated;
   a camera for taking an image of the pupil of the eye, and a computer, which is connected to the camera and executes a control program, for controlling the beam guidance mechanism in accordance with a treatment profile, the control program being designed in such a way that the computer ascertains during the treatment of the eye, on the basis of the image data supplied by the camera, a position of a specified point on the cornea of the eye and aligns the treatment profile relative to the thus ascertained position of the corneal point; and
   a computing device executing a control program, wherein the control program ascertains the position of the specified corneal point during the treatment of the eye taking account of a measured depth dimension of the eye to be treated, which depth dimension is representative of the depth of the anterior chamber and the thickness of the cornea; and
   wherein the control program ascertains the position of the specified corneal point during the treatment of the eye taking account of a rotational radius of the eye; and
   wherein the control program ascertains the position of the specified corneal point during the treatment of the eye taking account of a displacement of a center of the pupil relative to a reference position.

7. A method for controlling an apparatus for ophthalmological, refractive laser surgery, the apparatus being set up to route laser radiation onto or into the eye according to a spatial and time sequence that is determined by a desired treatment profile and that is aligned relative to a specified location of an eye to be treated, the method comprising:
   measuring a depth dimension of the eye to be treated at least once prior to the surgery, which depth dimension is representative of the depth of the anterior chamber and the thickness of the cornea;
   identifying a control point on a front surface of the cornea of the eye based on a center of the pupil of the eye as identified in image data representative of the eye obtained by an imaging device;
   determining a current location of the control point during the surgery by tracking the center of the pupil relative to a reference location to determine a displacement of the center of the pupil relative to the reference location and calculating the current location of the control point based on the displacement of the center of the pupil relative to the reference point and the depth dimension;

generating control program information that takes into account the current location of the control point; and routing laser radiation onto or into the eye to be treated based on the control program information.

8. The method of claim 7, wherein calculating the current location of the control point is further based on a rotational radius of the eye.

9. The method of claim 8, wherein the displacement of the center of the pupil is a rotational displacement.

10. The method of claim 7, wherein the imaging device that obtains the image data representative of the eye is a camera configured to obtain an image of the pupil and iris of the eye.

11. The method of claim 7, wherein the depth dimension is measured using an optical low coherence reflectometry device.

12. The method of claim 7, wherein an optical path of the optical low coherence reflectometry device is coaxial with a path of the laser radiation.

13. The method of claim 7, wherein the control point is the point at which the pupil axis pierces through the front surface of the cornea.

* * * * *